United States Patent [19]
Culross

[11] Patent Number: 6,090,742
[45] Date of Patent: Jul. 18, 2000

[54] PROCESS FOR THE PREPARATION OF HIGH ACTIVITY HYDROCARBON SYNTHESIS CATALYSTS; AND CATALYST COMPOSITIONS

[75] Inventor: Claude C. Culross, Baton Rouge, La.

[73] Assignee: Exxon Research and Engineering Company, Florham Park, N.J.

[21] Appl. No.: 08/845,017

[22] Filed: Apr. 22, 1997

[51] Int. Cl.[7] ...................... H01L 21/336; H01L 21/8228
[52] U.S. Cl. .......................... 502/258; 502/326; 502/327; 502/201; 502/260
[58] Field of Search .................................... 502/325, 326, 502/327, 201, 260, 258

[56] References Cited

U.S. PATENT DOCUMENTS

| 4,689,315 | 8/1987 | Anton et al. | 502/241 |
| 5,756,419 | 5/1998 | Chaumette et al. | 502/313 |

FOREIGN PATENT DOCUMENTS

| 7228798 | 9/1972 | France . |
| 949488 | 2/1964 | United Kingdom . |
| 1095008 | 12/1967 | United Kingdom . |

*Primary Examiner*—John F. Mebling
*Assistant Examiner*—Alexander G. Ghyka
*Attorney, Agent, or Firm*—Jay Simon; Jonathan N. Provoost

[57] ABSTRACT

A process for the preparation of a catalyst which is highly active for the synthesis of hydrocarbons from mixtures of hydrogen and carbon monoxide. A silica or silica-containing support is treated with a solution containing both an Iron Group metal, or metals, and nitrous acid, nitric acid, or a nitro-containing organo, or nitro-containing hydrocarbyl compound, or compounds, sufficient to hydroxylate the surface thereof and increase the number of hydroxyl groups on the surface of the support such that the metal component will be highly dispersed, this increasing the activity of the catalyst in a hydrocarbon synthesis reaction as contrasted with that of a catalyst of similar composition, similarly prepared except that the support component of the catalyst was not contacted and simultaneously treated with both the Iron Group metal and the acid.

17 Claims, No Drawings ions from the acid and water in the acid solution react with and open bridges on the surface of the support, hydroxylating the silica to form surface Si—OH functional groups, or surface sites on which the Iron Group metal, or metals, become more completely dispersed. The hydroxyl group functionality of a silica having initially very little, if any, hydroxyl groups attached to the silica surface, or a silica having a moderate to high number of hydroxyl groups attached to the silica surface, can in either event be increased by the acid treatment to act as sites for dispersion of metal crystallites; an increased number of metal crystallites translating into better metals dispersion and increased catalyst activity. For example, on impregnating a silica support with an aqueous solution of nitric acid and a cobalt compound, e.g., cobalt nitrate, the composite on calcination forms a catalyst which is more active in a hydrocarbon synthesis reaction than a catalyst of similar composition,
PROCESS FOR THE PREPARATION OF HIGH ACTIVITY HYDROCARBON SYNTHESIS CATALYSTS; AND CATALYST COMPOSITIONS

FIELD OF THE INVENTION

This invention relates to a process for the preparation of high activity Fischer-Tropsch catalysts; and high activity Fischer-Tropsch catalysts as compositions of matter.

BACKGROUND

Fischer-Tropsch synthesis, a process for the synthesis of hydrocarbons at elevated temperatures from mixtures of hydrogen and carbon monoxide contacted over a catalyst constituted of one or more Iron Group metals supported on a support or carrier, with or without added promoters, is well known. Generally, the catalyst is prepared by cogellation, coprecipitation, or impregnation techniques, typically by impregnation. In accordance therewith, a porous support or carrier, e.g., silica, is precalcined, contacted one or more times with an aqueous solution of a compound of the Iron Group metal, e.g., cobalt nitrate, and generally one or more times with an aqueous solution of a promoter, or promoters, e.g., a compound, or compounds of $ZrO_2$, $TiO_2$, Re, or a Group VIII noble metal. Alternatively, the precalcined support can be coimpregnated one or more times with a solution of a compound, or compounds of both the Iron Group metal compound and the promoter, or promoters. After the impregnation, or coimpregnation, the metal-containing support is dried to remove the liquid, calcined to convert the Iron Group metal to an oxide, and then reduced with hydrogen to convert the oxide components of the catalyst to metals. The precalcination and calcination steps are generally carried out at temperatures ranging from about 250° C. to about 600° C., or higher, for sustained periods. Whereas catalysts made at an earlier date which did not contain the promoter generally possessed good $C_5^+$ selectivity, the activity of the catalyst in conducting a Fischer-Tropsch reaction was relatively low. The addition of the promoter generally increased the activity of the catalyst while the catalyst retained its selectivity. Albeit the later catalysts possessed relatively good activity, Fischer-Tropsch catalysts of yet higher activity are needed to meet the demands of the commercial world.

THE INVENTION

This invention, accordingly, relates to a process for the preparation of a catalyst by treating a silica, or silica-containing support with a solution containing an Iron Group metal of the Periodic Table of the Elements (Sargent-Welch Scientific Company, Chicago, Ill., Copyrighted 1968), e.g., iron, cobalt, nickel or mixtures of two or more of these metals with each other, or mixture of one or more of the Iron Group metals with other metals, and nitrous acid, nitric acid, or a nitro-containing organo, or nitro-containing hydrocarbyl compound, or compounds, sufficient to hydroxylate the surface of the support and composite said metal, or metals, with the surface hydroxylated silica support. Preferably, the silica, or silica-containing support, is treated with the solution at sufficiently low pH to produce a hydroxylated support surface; a surface on which the Iron Group metal, or metals, is highly dispersed. A preferred catalyst is one comprised of cobalt and a hydroxylated silica, or silica-containing support, on which the cobalt is dispersed.

In general, an increase in catalyst activity is obtained by an increase in metals dispersion, given similar catalysts with similar metals loadings. It has been found, in accordance with this invention, that the dispersion of catalysts is increased by the amount of hydroxyl groups contained on the surface of the silica, or silica-containing support, with which the Iron Group metal, or metals, is combined during catalyst preparation. The greater the number of hydroxyl groups formed per unit area of support surface by treatment with the acid, or acid compounds (which can range up to and including about seven (7) hydroxyl groups per $nm^2$ ($nanometer^2$), this constituting a substantially fully hydroxylated surface), the greater the dispersion of the metals in a finished catalyst, given similar catalysts with similar metal, and metals loadings. For example, a cobalt-silica catalyst made by compositing cobalt with a commercially supplied silica treated with nitrous acid, nitric acid, or an acidic nitro-containing organo, or nitro-containing hydrocarbyl compound, or compounds, e.g., nitric acid, to catalyze addition of hydroxyl groups to the surface of this silica has been found to be fully as active as a rhenium promoted cobalt-silica catalyst similar to the former except that the catalyst was promoted with an added quantity of rhenium, and the silica support from which the catalyst was made was not treated with the acid to hydroxylate the support surface. Study, and comparisons made between the two catalysts show that the catalyst made from the support having the hydroxyl functionality supplied by the acid is fully the equivalent in activity to the catalyst supplied with the rhenium promoter for activation of the catalyst; rhenium being an important, albeit an extremely expensive and rare metal for use in this capacity. In the preparation of the catalyst, the support is impregnated with a solution of the nitrous acid, nitric acid, or an acidic nitro-containing organo, or nitro-containing hydrocarbyl compound, or compounds, e.g., nitric acid, and a compound of the Iron Group metal, e.g., cobalt nitrate. The support, impregnated with both the acid and the compound of the Iron Group metal, is then heated at low temperature and dried; preferably at temperatures ranging to about 110° C., more preferably from about 80° C. to about 110° C., over a period ranging up to about 24 hours, preferably for a period ranging from about 16 hours to about 18 hours. The Iron Group metal-containing catalyst is then calcined at temperatures ranging up to about 500° C., preferably up to about 300° C.; suitably by staging. For example a catalyst brought from ambient temperature up to about 300° C. over a period of about one-quarter of an hour to about 3 hours, and this temperature held for an additional period sufficient to substantially decompose the cobalt nitrate and form $Co_3O_4$, has been found to have high activity.

In the preparation of the support by contact and treatment with the acid, $H^+$ ions from the acid and water in the acid solution react with and open bridges on the surface of the support, hydroxylating the silica to form surface Si—OH functional groups, or surface sites on which the Iron Group metal, or metals, become more completely dispersed. The hydroxyl group functionality of a silica having initially very little, if any, hydroxyl groups attached to the silica surface, or a silica having a moderate to high number of hydroxyl groups attached to the silica surface, can in either event be increased by the acid treatment to act as sites for dispersion of metal crystallites; an increased number of metal crystallites translating into better metals dispersion and increased catalyst activity. For example, on impregnating a silica support with an aqueous solution of nitric acid and a cobalt compound, e.g., cobalt nitrate, the composite on calcination forms a catalyst which is more active in a hydrocarbon synthesis reaction than a catalyst of similar composition, similarly prepared except that nitric acid is not impregnated into the support. The reason for this, it is believed, is due to the larger number of hydroxyl sites formed on the surface of the former, which transform by interaction with the cobalt into a greater number of catalytically active metal sites, i.e., better dispersion of the metal upon the silica support surface.

Nitrous acid, nitric acid, or a nitro-containing organo, or nitro-containing hydrocarbyl compound, or compounds, dissolved in aqueous solution can supply the $H^+$ ion or hydronium ion, $H_3O^+$, to catalyze the hydroxylation of the surface of the silica. Nitric acid is particularly preferred because of its strongly acidic character, wide availability and high cost effectiveness. Nitrated organic acids, whether substituted or unsubstituted, saturated or unsaturated, straight chain, branched chain, cyclic or aromatic, can also be used as hydroxylating agents. Exemplary of acids of this type are nitrated alphatic hydrocarbon compounds, particularly those containing from 1 to about 6 carbon atoms in the molecule, exemplary of which is trinitromethane, 2-nitropropane and the like; mono- or polyaromatic compounds containing from about 6 to about 20 carbon atoms in the molecule where one or more hydrogen atoms on an aromatic nucleus has been replaced by a nitro ($\cdot NO_2$), or nitro groups, e.g., trinitrophenol (picric acid), dinitrophenols, nitronaphthols, nitroanthrols, and the like. The selected acid is dispersed, or dissolved in a liquid, preferably water, with a compound of the Iron Group metal, or metals, and the silica, or silica-containing support is then contacted with the solution to impregnate the pores of the support and deposit the metal, or metals, therein. Generally, the acid is dissolved in the liquid in concentration sufficient to form a solution of pH ranging from about −1 to about 3, preferably from about 0 to about 1; this corresponding to a molarity ranging from about 10 M to about 0.001 M, preferably from about 1.0 M to about 0.1 M. Suitably, with conventional size, formed supports with essentially 100% internal surface area, preferably from about 0.01 to about 10 times, more preferably from about 0.05 to about 1.0 times the total pore volume of the support, of the acid solution is added to the support to impregnate the silica or silica-containing support. The time of contact between the support and the solution generally ranges from about 0.02 hour to about 10 hours, preferably from about 0.1 hour to about 6 hours. The catalyst, or metals-containing support, after treatment is then dried, and calcined, to produce a catalyst which is more active in synthesizing hydrocarbons than a catalyst of similar composition, similarly prepared except that the support is not treated with the acid. Also, it is more active than a catalyst which has been sequentially acid treated, and the metal, or metals, then deposited on the support in a subsequent step.

The Iron Group metal, iron, cobalt, or nickel, preferably cobalt, is dispersed with the acid on the silica or silica-containing support in catalytically effective amount. Suitably, in terms of absolute concentration, the metal is dispersed on the support in amount ranging from about 1 percent to about 60 percent, preferably from about 15 percent to about 50 percent, based on the total weight of the catalyst composition (dry basis, metal oxide form). The metal is composited with a powder, or previously pilled, pelleted, beaded, extruded or sieved support, preferably by the impregnation method. The metal, e.g., cobalt, is composited with the support by contacting the support with an acid solution which contains the cobalt-containing compound, or salt, e.g., a nitrate, carbonate or the like. If desired, a promoter, e.g., platinum, palladium, rhenium, or the like, can be added to the solution. Salts of the Iron Group metal, or the promoter metal, may be dissolved with the acid in any suitable solvent, e.g., water, hydrocarbon solvent, or mixtures thereof. The amount of impregnation solution used should be adequate to completely immerse the support, usually within a range of about 1 to 20 times the volume of the support. In the incipient wetness technique, the entire solvent which contains a precisely measured amount of the metal, or metals, is adsorbed by the support. The impregnation treatment can be carried out under a wide range of conditions including ambient or elevated temperatures.

The support employed in the practice of this invention is silica, or silica-containing support, natural or synthetic. The support contains at least about 33 percent silica, preferably at least about 90 percent silica, more preferably about 100 percent silica, based on the total weight of the support (dry basis). The support however can contain the oxides of other metals, i.e., from Groups II, III, IV, V and VIB of the Periodic Table of the Elements; especially from Groups IIA, IIIA and IVB. Exemplary of such oxides are alumina, boria, zinc oxide, magnesia, calcium oxide, barium oxide, titania, zirconia, $TiO_2$—$SiO_2$, $ZrO_2$—$SiO_2$ combinations, and the like.

Precalcination, or calcination, and even drying of the support prior to addition of the solution containing the metal, or metals, to the support is undesirable, and is generally to be avoided unless needed to reduce impurities, or to create additional pore volume for incipient wetness impregnation by removing water. Calcination of the support, even drying at moderate temperatures, can reduce the number of hydroxyl sites which are present on the surface of the supports; a factor which will reduce the activity of the finished catalyst by reducing dispersion. The support, prior to impregnation with the solution containing the metal, or metals, may be air dried, or warmed and dried, in the presence of nitrogen or oxygen, or both, in an air stream or under nitrogen, or azeotropically dried, at temperatures below 100° C. However, temperatures as high as 100° C. can over a short period of treatment reduce the amount of hydroxyl groups on the support surface; and the amount of activity imparted to the catalyst. The practice of this invention reverses the loss of hydroxyl groups which occurs during precalcination or drying.

After impregnation of the support with the solution of the acid and metal, or metals, the catalyst is calcined, or dried and then calcined. Preferably, the catalyst is contacted with an oxygen-containing gas, e.g., air or oxygen, dried and calcined at temperature sufficient to oxidize the Iron Group metal, e.g., cobalt, and convert the cobalt to $Co_3O_4$. Temperature ranging above about 150° C., preferably above about 200° C., and up to about 300° C. is generally satisfactory to oxidize the cobalt. Thereafter the metal oxide, or metal oxides, are reduced suitably by contact of the catalyst with hydrogen or hydrogen-containing gas at temperature above about 200° C., preferably above about 250° C. for periods ranging from about 0.5 hour to about 24 hours, at pressures ranging from about ambient to about 40 atmospheres.

The following non-limiting examples, and comparative data, are exemplary of the invention.

In the following examples, and demonstrations, the $O_2$ chemisorption values of the catalysts was determined as follows: A precisely known weight of catalyst falling within the range of 0.075–0.100 g was loaded into a U-shaped reactor mounted in an Infra-red furnace. The catalyst was heated to 225° C. at a rate of 3.4° C./min under $H_2$ at a flow of 100 cc/min. The catalyst was not held at that temperature, but was heated to 450° C. over the next 60 min. The catalyst was activated by holding at 450° C. for 100 min. After the hold time, $H_2$ flow was cut out and replaced by He at 40 cc/min. The reactor was cooled to ambient temperature, and held under flowing He for an additional 30–45 min after reaching ambient temperature. Next the catalyst was dosed with precise, individual 5 cc pulses of 10% $O_2$/He at 1.5–2.0 min intervals for 2 hours. A TCD Gas Chromatograph was used to monitor and measure $O_2$ breakthrough from the catalyst bed. $O_2$ uptake by catalyst was calculated by difference between the dosed and breakthrough amounts in units of micromoles $O_2$ per gram of catalyst.

The first example presented directly below shows that a CoRe/$SiO_2$ catalyst made by a single impregnation of a silica support with a solution containing both the catalytic metals and the acid possesses a high oxygen chemisorption value, a value known to correlate well with catalyst activity; the higher the oxygen chemisorption value, the higher the catalyst activity.

EXAMPLE 1

A standard aqueous solution of metal compounds was made which consisted of 171.02 g $Co(NO_3)_2.6H_2O$, 5.94 ca. 65 wt % aqueous $HReO_4$, and 38.36 g 1M $HNO_3$. This was designated as Solution A.

5 g of EH-5 Cab-O-Sil (Cabot Corporation) was mixed with 30.22 g Solution A, dried in a vacuum oven overnight at ca. 110° C., and ground to a powder. The powder was calcined in temperature/time stages at 125° C./30 min, 150° C./60 min, and 300° C./60 min. This was designated as Catalyst A, and contained 40.40 wt % Co.

After reduction at 450° C./100 min, Catalyst A was found to have an $O_2$ uptake of 2028 micromoles $O_2$ per gram of catalyst. Or, in other words, Catalyst A was found to have an oxygen chemisorption value of 2028 $\mu$mol $O_2$/g catalyst after reduction of the catalyst at 450° C.

The following, in contrast, demonstrates that CoRe/$SiO_2$ catalysts made by sequential impregnations of a silica support, first with the acid and then with the catalytic metals, have lower oxygen chemisorption values than the catalyst of Example 1. In a first of two demonstrations, nitric acid is added in a first stage, and $Co(NO_3)_2.6H_2O$/$HReO_4$ is added in a second stage, the amount of acid added in the first stage being equal to the amount of acid used in Example 1.

Demonstration One (D-1)

A standard aqueous solution of metal compounds was made which consisted of 171.03 g $Co(NO_3)_2.6H_2O$, 5.96 g ca. 65 wt % aqueous $HReO_4$, and 36.05 g $H_2O$. The mixture was gently heated to drive the solid $Co(NO_3)_2.6H_2O$ into solution and cooled to room temperature before use. This was designated as Solution B.

EH-5 Cab-O-Sil was sequentially impregnated with aqueous $HNO_3$ and Solution B with intermediate drying between impregnations. 10 g of EH-5 was first mixed with 10.77 g 1M $HNO_3$ and dried in a vacuum oven overnight at ca. 110° C. The amount of $HNO_3$ used here mimics the amount of $HNO_3$ present in Solution A to make Catalyst A in Example 1. After drying, 5 g of $HNO_3$-treated EH-5 was impregnated with 29.90 g Solution B, dried in a vacuum oven overnight at ca. 110° C., and ground to a powder. The powder was calcined in temperature/time stages at 125° C./30 min, 150° C./60 min, and 300° C./60 min. This was designated as Catalyst B, and contained 39.70 wt % Co.

After reduction at 450° C./100 min, Catalyst B was found to have an $O_2$ uptake of 1928 micromoles $O_2$ per gram of catalyst.

Demonstration Two (D-2)

EH-5 Cab-O-Sil was sequentially impregnated with aqueous $HNO_3$ and Solution B with intermediate drying between impregnations. 10 g of EH-5 was first mixed with 24.42 g 1M $HNO_3$ and dried in a vacuum oven overnight at ca. 110° C. The amount of $HNO_3$ was sufficient to completely wet the EH-5. After drying, 5 g of $HNO_3$-treated EH-5 was impregnated with 29.89 g Solution B, dried in a vacuum overnight at ca. 110° C., and ground to a powder. The powder was calcined in temperature/time stages at 125° C./30 min, 150° C./60 min, and 300° C./60 min. This was designated as Catalyst C, and contained 40.08 wt % Co.

After reduction at 450° C./100 min, Catalyst C had an $O_2$ uptake of 1547 micromoles $O_2$ per gram of catalyst.

The data presented by Example 1, contrasted with demonstrations one and two, thus clearly show that CoRe/$SiO_2$ catalysts made by a single impregnation of a silica support with a solution containing both the catalytic metals and the acid is superior in activity to catalysts of otherwise similar composition, but made by sequential impregnation with the acid and catalytic metals, respectively.

The following Example 2 shows that a cobalt-silica catalyst, Co—$SiO_2$, made pursuant to the practice of this invention is more active than a rhenium promoted cobalt-silica catalyst, CoRe—$SiO_2$, wherein the rhenium was supplied by the addition of $HReO_4$ to the solution.

EXAMPLE 2

A standard aqueous solution of metal compound was made which consisted of 171.00 g $Co(NO_3)_2.6H_2O$ and 38.37 g 1M $HNO_3$. This was designated as Solution C.

10 g of EH-5 Cab-O-Sil was mixed with 60.43 g Solution C, dried in a vacuum oven overnight at ca. 110° C., and ground to a powder. The powder was calcined in temperature/time stages at 125° C./30 min, 150° C./60 min, and 300° C./60 min. This was designated as Catalyst D, and contained 43.75 wt % Co and 0.25 wt % N.

After reduction at 450° C./100 min, Catalyst D had an $O_2$ uptake of 2214 micromoles $O_2$ per gram of catalyst.

The following demonstrates the activity of a CoRe/$SiO_2$ catalyst as contrasted with the activity of the non-rhenium promoted Co/$SiO_2$ catalyst described by Example 2.

Demonstration 3 (D-3)

A standard aqueous solution of metal compounds was made which consisted of 373.09 g $Co(NO_3)_2.6H_2O$, 12.96 g ca. 65 wt % aqueous $HReO_4$, and 78.56 g $H_2O$. The mixture was gently heated to drive the solid $Co(NO_3)_2.6H_2O$ into solution, and cooled to room temperature before use. This was designated as Solution D.

10 g of EH-5 Cab-O-Sil was mixed with 59.77 g Solution D, dried in a vacuum oven overnight at ca. 110° C., and ground to a powder. The powder was calcined in temperature/time stages at 125° C./30 min, 150° C./60 min, and 300° C./60 min. This was designated as Catalyst E, and contained 38.83 wt % Co and 0.15 wt % N.

After reduction at 450° C./100 min, Catalyst E had an $O_2$ uptake of 1880 micromoles $O_2$ per gram of catalyst.

The table below summarizes the oxygen chemisorption results obtained in each of the examples, and demonstrations. The first column of the Table identifies the specific example, or demonstration, and identifies the catalyst; the second column indicates whether or not nitric acid was employed in the catalyst preparation; the third column identifies the stage in which the nitric acid was employed; and column 4 lists the oxygen chemisoption values which were obtained.

| Example/ or Demonstration Identity of Catalyst | HNO₃ | Stage HNO₃ applied | O₂ Chemisorption Value ($\mu$mol O₂/g cat after 450° C. Reduction) |
| --- | --- | --- | --- |
| Example 1 (Catalyst A) | Yes | w/Co-Re | 2028 |
| Demonstration 1 (Catalyst B) | Yes | First of 2 Stages | 1928 |
| Demonstration 2 (Catalyst C) | Yes | First of 2 Stages | 1547 |
| Example 2 (Catalyst D) | Yes | Applied w/Co; No Re | 2214 |
| Demonstration 3 (Catalyst E) | No | Co-Re only | 1880 |

It is apparent that various modifications and changes can be made without departing the spirit and scope of the invention.

Having described the invention, what is claimed is:

1. A process for the preparation of a highly active catalyst for the synthesis of hydrocarbons from mixtures of hydrogen and carbon monoxide which comprises contacting and treating a preformed silica or silica-containing support with a solution containing both a cobalt metal compound and a compound selected from the group consisting of nitrous acid, nitric acid, and an acidic nitro-containing hydrocarbyl compound, or compounds, sufficient to hydroxylate the surface of the support, increase the number of hydroxyl groups on the surface of the support, and composite in finely dispersed form the cobalt metal compound on the support surface, calcining the treated support, and contacting the calcined support with hydrogen at a temperature above 200° C., such that the activity of the catalyst is greater in a hydrocarbon synthesis reaction than a catalyst of similar composition, similarly prepared except that the support component of the catalyst was not contacted and treated with the acid; or was treated with the acid and cobalt compound in sequential steps.

2. A highly active catalyst for the synthesis of hydrocarbons from mixtures of hydrogen and carbon monoxide which comprises a preformed silica or silica-containing support which has been contacted and treated with a solution containing both a cobalt metal compound and a compound selected from the group consisting of nitrous acid, nitric acid, and an acidic nitro-containing hydrocarbyl compound, or compounds, sufficient to hydroxylate the surface of the support, increase the number of hydroxyl groups on the surface thereof, and composite in finely dispersed form the cobalt metal compound on the support surface, the support is calcined and the calcined support is contacted with hydrogen at a temperature above 200° C., such that the activity of the catalyst is greater in a hydrocarbon synthesis reaction than a catalyst of similar composition, similarly prepared except that the support component of the catalyst was not contacted and treated with the acid, or was treated with the acid and the cobalt metal compound in sequential steps.

3. The process of claim 1 wherein the acid is nitric acid.

4. The process of claim 1 wherein the Iron Group metal is cobalt, the acid is nitric acid, and the support consists essentially of silica.

5. The process of claim 1 wherein the Iron Group metal component of the catalyst is cobalt, and the acid contacted with the surface of the support is a nitric acid.

6. The process of claim 5 wherein the solution containing the Iron Group metal compound and the acid used to treat the silica support is of pH ranging from about −1 to about 3.

7. The process of claim 6 wherein the pH of the solution ranges from about 0 to about 1.

8. The composition of claim 2 wherein the acid is nitric acid.

9. The composition of claim 2 wherein the Iron Group metal is cobalt, the acid is nitric acid, and the support consists essentially of silica.

10. The composition of claim 2 wherein the solution containing the Iron Group metal compound and the acid used to treat the silica support is of pH ranging from about −1 to about 3.

11. The composition of claim 10 wherein the pH of the solution ranges from about 0 to about 1.

12. The composition of claim 10 wherein the time of treatment of the support with the solution ranges from about 0.02 hour to about 10 hours.

13. The composition of claim 10 wherein the time of treatment of the support with the solution ranges from about 0.1 hour to about 6 hours.

14. The process of claim 1 wherein the acid is nitric acid, the support contains at least 33 percent silica, based on the total weight of the support (dry basis), the pH of the solution containing the cobalt compound ranges from about −1 to about 3, and the time of the treatment ranges from about 0.02 hour to about 10 hours.

15. The process of claim 6 wherein the time of treatment of the support with the solution ranges from about 0.02 hour to about 10 hours.

16. The process of claim 15 wherein the time of treatment of the support with the solution ranges from about 0.1 hour to about 6 hours.

17. The composition of claim 2 wherein the acid in nitric acid, the support contains at least 33 percent silica, based on the total weight of the support (dry basis), the pH of the solution containing the cobalt comprised ranges from about −1 to about 3, and the time of the treatment ranges from about 0.02 hour to about 10 hours.

* * * * *